(12) United States Patent
Hammock et al.

(10) Patent No.: US 9,850,207 B2
(45) Date of Patent: Dec. 26, 2017

(54) SUBSTITUTED PIPERIDINES AS SOLUBLE EPDXIDE HYDROLASE INHIBITORS

(71) Applicant: The Regents of the University of California, Oakland, CA (US)

(72) Inventors: Bruce D. Hammock, Davis, CA (US); Kin Sing Lee, Davis, CA (US); Bora Inceoglu, Davis, CA (US); Karen Wagner, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/375,704

(22) PCT Filed: Feb. 1, 2013

(86) PCT No.: PCT/US2013/024429
§ 371 (c)(1),
(2) Date: Jul. 30, 2014

(87) PCT Pub. No.: WO2013/116713
PCT Pub. Date: Aug. 8, 2013

(65) Prior Publication Data
US 2015/0065540 A1    Mar. 5, 2015

Related U.S. Application Data

(60) Provisional application No. 61/593,811, filed on Feb. 1, 2012.

(51) Int. Cl.
*C07D 211/58*   (2006.01)
*C07D 211/96*   (2006.01)
*A61K 31/4468*  (2006.01)

(52) U.S. Cl.
CPC ........ *C07D 211/96* (2013.01); *A61K 31/4468* (2013.01); *C07D 211/58* (2013.01)

(58) Field of Classification Search
CPC .................................................... C07D 211/58

USPC .......................................................... 546/244
See application file for complete search history.

(56) References Cited

U.S. PATENT DOCUMENTS

| 8,399,425 | B2 | 3/2013 | Hammock et al. |
| 2007/0149512 | A1 | 6/2007 | Antel et al. |
| 2008/0221100 | A1* | 9/2008 | Gless .................. C07D 211/58 514/235.5 |
| 2009/0247521 | A1 | 10/2009 | Aavula et al. |
| 2010/0267807 | A1 | 10/2010 | Hammock et al. |

FOREIGN PATENT DOCUMENTS

WO    WO 2009/086426 A2    7/2009

OTHER PUBLICATIONS

Jordan, V. C. Nature Reviews: Drug Discovery, 2, 2003, 205.*
Schebb, et al. Analytical and Bioanalytical Chemistry, 400(5), 2011, 1359-1366.*
Hackam, et al. JAMA, 296(14), 2006, 1731-1732.*
Shen, Hong C. et al.: "*Discovery of Inhibitors of Soluble Epoxide Hydrolase: A Target with Multiple Potential Therapeutic Indications*"; Journal of Medicinal Chemistry, vol. 55:5, Mar. 8, 2012, pp. 1789-1808.
Extended European Search Report, dated Jun. 9, 2015, regarding EP 13 74 3566.

* cited by examiner

*Primary Examiner* — Douglas M Willis
(74) *Attorney, Agent, or Firm* — DLA Piper LLP (US)

(57) ABSTRACT

Provided are methods for treating, reducing, alleviating, and/or inhibiting neuropathic pain by orally, intravenously or intrathecally administering an effective amount of an inhibitor of soluble epoxide hydrolase ("sEH"), to a patient in need thereof. The neuropathic pain treated is selected from the group consisting of post-herpetic neuralgia, trigeminal neuralgia, focal peripheral nerve injury, and anesthesia dolorosa, central pain due to stroke or mass lesion, spinal cord injury, or multiple sclerosis, and peripheral neuropathy due to diabetes, HIV, or chemotherapy.

8 Claims, 16 Drawing Sheets

| | $K_i$ | $IC_{50}$ (tDPPO) |
|---|---|---|
|  | 16 | 440 |
|  | 0.98 | 15 |
|  | 0.26 | 9.5 |

| | Rat sEH $IC_{50}$ (EET) | Human sEH $IC_{50}$ (EET) |
|---|---|---|
|  | 1241 | 4957 |
|  | 411 | 842 |
|  | TBA | 226 |

Oral dose of 0.3 mg/kg each compound.

| 14,15 EETs Assay | | IC50 (nM) | | |
| --- | --- | --- | --- | --- |
| sEHI | Structure | Rat | Mouse | Human |
| 2389 |  | 685 | | 484 |
| 2372 |  | 697 | | 363 |
| 2414 |  | 411 | | 842 |
| 700 |  | | | 191 |

SUBSTITUTED PIPERIDINES AS SOLUBLE EPDXIDE HYDROLASE INHIBITORS

CROSS-REFERENCES TO RELATED APPLICATIONS

This application is a 35 USC §371 National Stage application of International Application No. PCT/US2013/024429 filed Feb. 1, 2013, now pending; which claims the benefit under 35 USC §119(e) to U.S. Application Ser. No. 61/593,811 filed Feb. 1, 2012. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This invention was made with government support under Grant No. ES002710 awarded by the National Institute of Environmental Health Sciences. The government has certain rights in the invention.

BACKGROUND OF THE INVENTION

Pain is generally divided into nociceptive and neuropathic pain. Nociceptive pain stems from neural pathways in response to tissue damaging or potentially tissue damaging signals, and includes inflammatory pain. Neuropathic pain tends to relate to dysfunctions within the nervous system. Unfortunately, agents that treat one kind of pain do not necessarily treat the other. Anti-inflammatory agents, for example, do not relieve the "phantom limb" pain felt by amputees.

In mammals, inflammatory pain is driven primarily by arachidonic acid (sometimes abbreviated as "AA"). Inflammatory pain develops as a result of tissue injury such as a cut or a bacterial infection upon which a large amount of AA is released at the site of injury by the actions of phospholipases. Synchronized to this event is the upregulation of cyclooxygenase-2 (COX-2), an enzyme which converts the released AA to prostaglandins, potent pain producing molecules. Released AA is metabolized by cyclooxygenases ("COX"), lipoxygenases ("LOX") and cytochrome P450 epoxygenases to yield prostaglandins, leukotrienes and epoxy-eicosatrienoic acids ("EETs") respectively. These materials may be further metabolized, for example they may be converted to bioactive amides and conjugates. Inflammatory pain is well correlated with the production of Cox-2 metabolites of AA, the prostaglandin series molecules. Consequently, a profound decrease in pain follows the inhibition of the inducible Cox-2, which is often attributed to the reduction of $PGE_2$, a key regulator.

In contrast, in neuropathic pain, there is little evidence of an inflammatory process mediated by arachidonic acid, cyclooxegenases and prostaglandins. Neuropathic pain is caused by a lesion of the peripheral or central nervous system (or both) manifesting with sensory symptoms and signs. Underlying causes include infections, trauma, metabolic abnormalities, chemotherapy, surgery, irradiation, neurotoxins, inherited neurodegeneration, nerve compression and tumor infiltration. Mechanisms of neuropathic pain are described, for example, in Zhuo, *Molecular Pain* (2007) 3:14; Campbell and Meyer, *Neuron* (2006) 52(1):77-92; Dworkin, et al., *Arch Neurol* (2003) 60:1524-34.

The pharmacological agents that have must commonly been shown to effectively block neuropathic pain are tricyclic anti-depressants (TCAs). However these agents are not effective at all in some patients and are only partially effective in others. Therefore the therapy of neuropathic pain is an unmet and growing clinical need. TCAs have many disadvantages well known in the field. Since neuropathic pain is a debilitating and hard to treat condition, however, TCAs have been used despite their disadvantages in the absence of agents with less adverse effects.

What is needed are compounds that can treat neuropathic pain. Surprisingly, the present invention meets this and other needs.

BRIEF SUMMARY OF THE INVENTION

The present invention provides methods for treating, reducing, alleviating, and/or inhibiting neuropathic pain by administration of an inhibitor of soluble epoxide hydrolase ("sEH"), to a patient in need thereof.

Accordingly, in one aspect, the invention provides methods for relieving neuropathic pain in a subject in need thereof, said method comprising administering to said subject an effective amount of an inhibitor of soluble epoxide hydrolase ("sEH"), thereby relieving said neuropathic pain in said subject.

In some embodiments, the neuropathic pain is selected from the group consisting of post-herpetic neuralgia, trigeminal neuralgia, focal peripheral nerve injury, and anesthesia dolorosa, central pain due to stroke or mass lesion, spinal cord injury, or multiple sclerosis, and peripheral neuropathy due to diabetes, HIV, or chemotherapy.

In some embodiments, the neuropathic pain is chronic. In some embodiments, the subject is experiencing the neuropathic pain.

In some embodiments, the agent is administered orally. In some embodiments, the agent is administered intravenously. In some embodiments, the agent is administered intrathecally. In some embodiments, the agent is delivered directly to a damaged nerve.

In some embodiments, the neuropathic pain is central neuropathic pain. In some embodiments, the neuropathic pain is peripheral neuropathic pain.

In some embodiments, the subject or patient is a human.

DETAILED DESCRIPTION OF THE INVENTION

I. General

Figure 1:
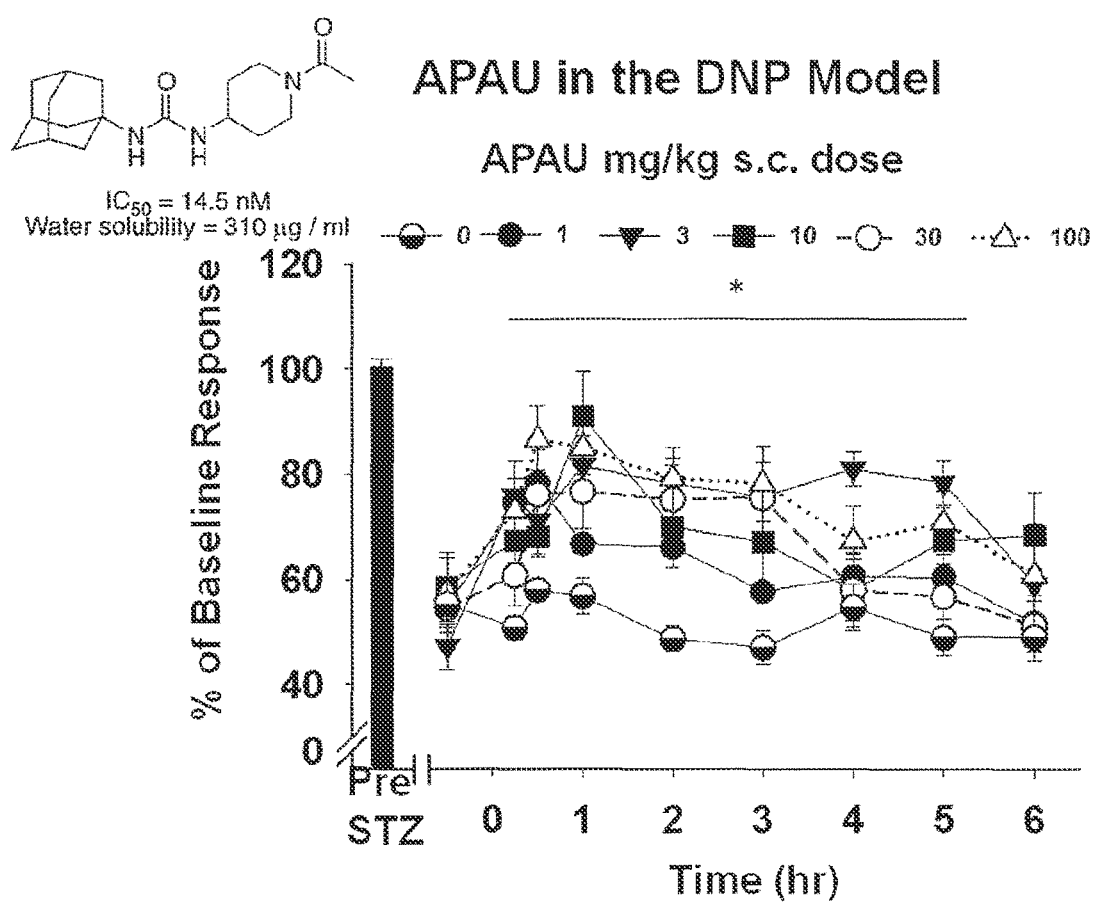
FIG. 1 shows dose (0, 1, 3, 10, 30, 100 mg/kg (mpk)) and time dependency of effect of UC1153 (APAU) on streptozocin (STZ)-induced type I diabetes model of neuropathic pain in rats where below 60% of baseline is painful state and 100% of baseline is lack of enhanced pain detection. (Result is an average of 6 rats.)
Figure 2:
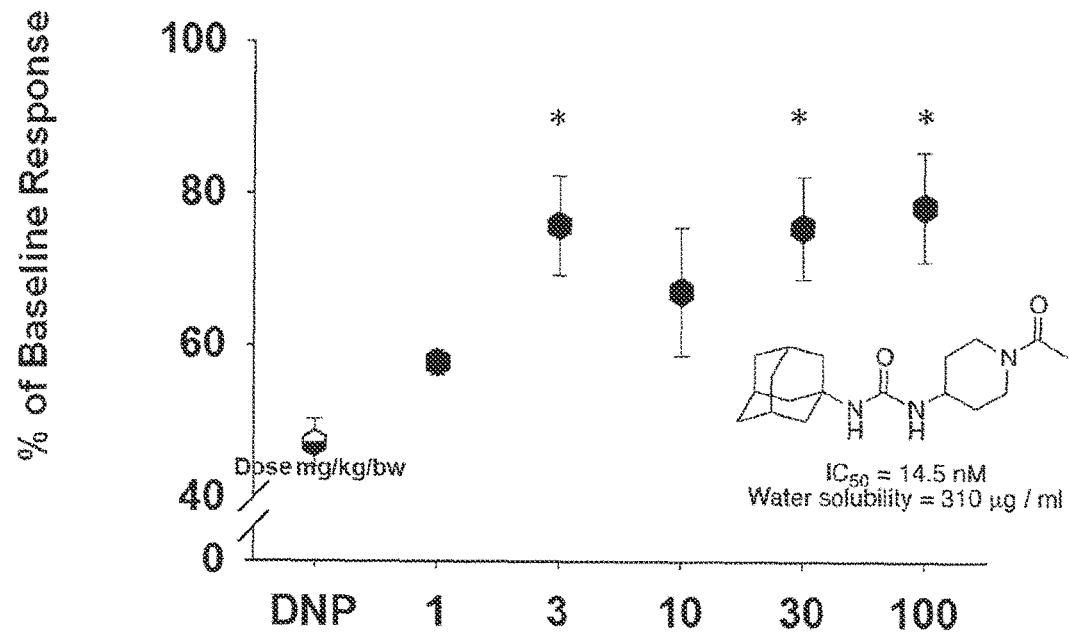
FIG. 2 shows dose response curve (% of Baseline response) of UC1153 on streptozocin (STZ)-induced type I diabetes model of neuropathic pain in rats at hour 3 where below 60% of baseline is painful state and 100% of baseline is lack of enhanced pain detection. (Result is an average of 6 rats.)
Figure 3:
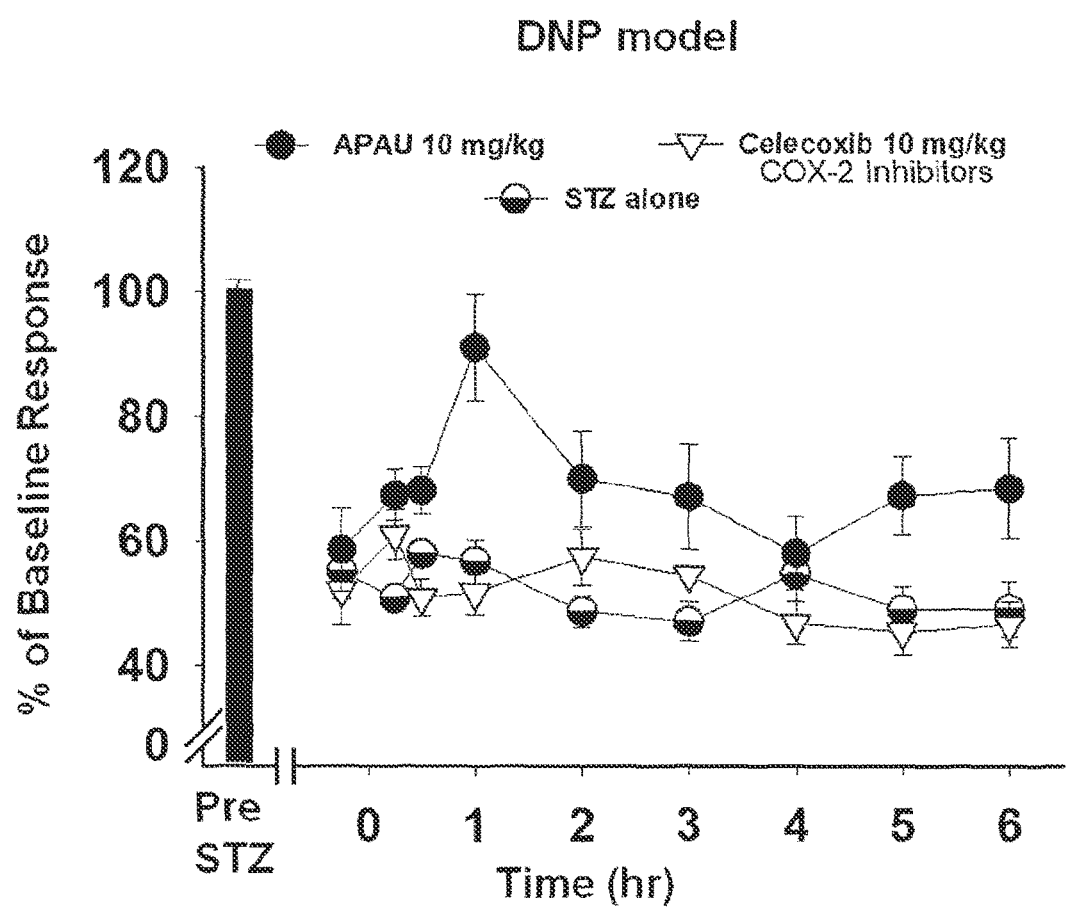
FIG. 3 shows dose and time dependency of UC1153 (10 mpk) and celecoxib (10 mpk) on streptozocin (STZ)-induced type I diabetes model of neuropathic pain in rats streptozocin (STZ)-induced type I diabetes model of neuropathic pain in rats where below 60% of baseline is painful state and 100% of baseline is lack of enhanced pain detection. (Result is an average of 6 rats). 10 mpk of UC1153 can significantly alleviate the pain response of streptozocin (STZ)-induced type I diabetes rat model of neuropathic pain as compared to 10 mpk of celecoxib.
Figure 4:
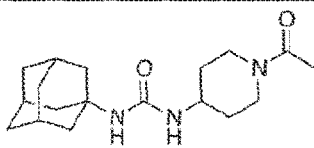
FIG. 4 shows Inhibition constant ($K_i$) and $IC_{50}$ of inhibitors from radiometric assay (tDPPO) against human sEH (top table); bottom table shows $IC_{50}$ of inhibitors from LC/MS-MS assay (EET) against rat sEH and human sEH.
Figure 4:
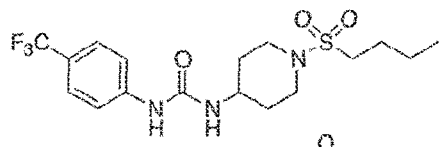
Figure 4:
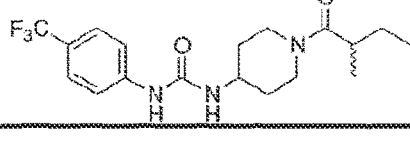
Figure 4:
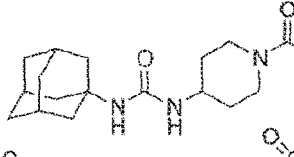
Figure 4:
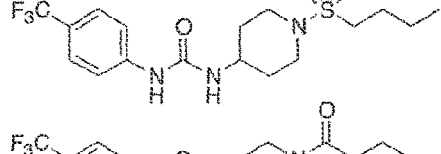
Figure 4:
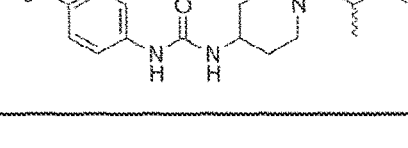
Figure 5:
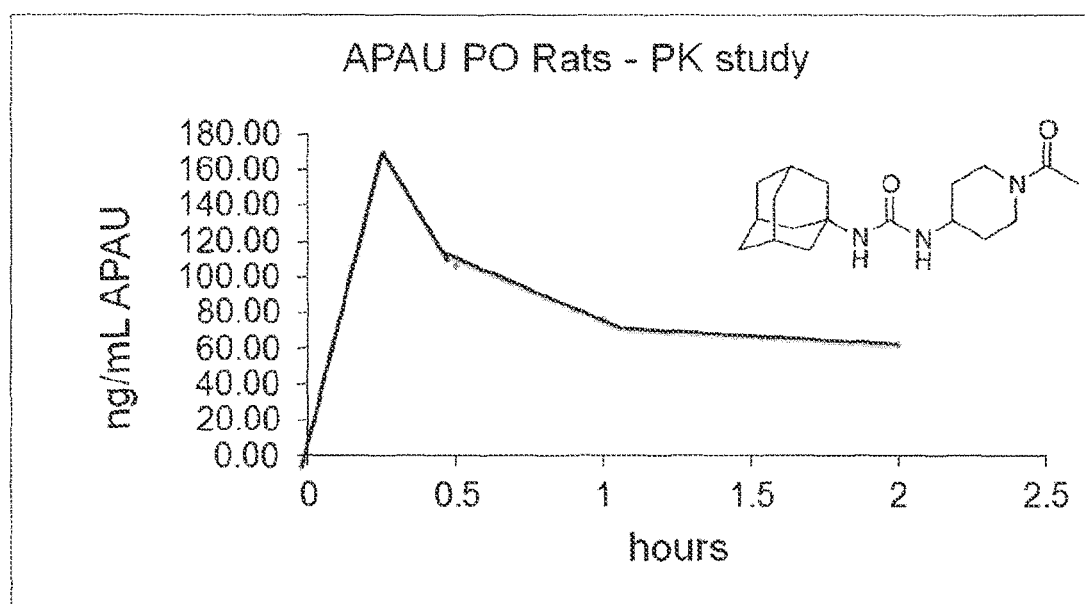
FIG. 5 shows pharmacokinetic Profile of UC1153 (APAU) at 10 mpk with rat. Rats are treated with UC1153 by oral gavage. UC1153 was dissolved in 20% PEG in oleic acid-rich triglyceride. The result is an average of 6 rats.
Figure 6:
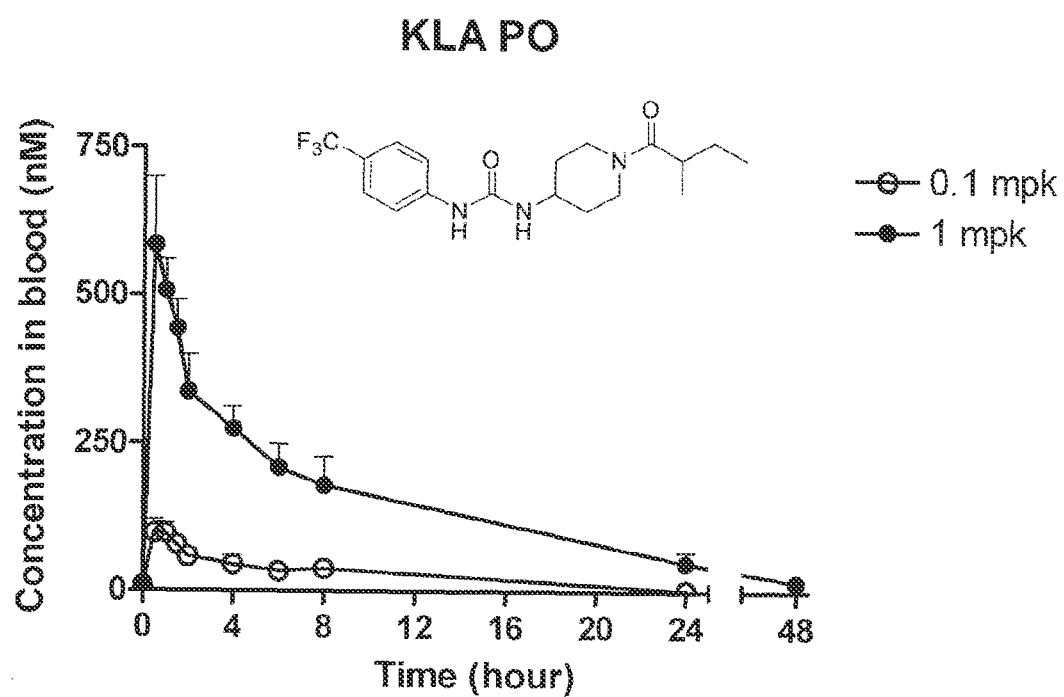
FIG. 6 shows pharmacokinetic Profile of UC2383 (KLA) in rat. Rats are treated with UC2383 by oral gavage. UC2383 was dissolved in 20% PEG in oleic acid-rich triglyceride. The result is an average of 6 rats.
Figure 7:
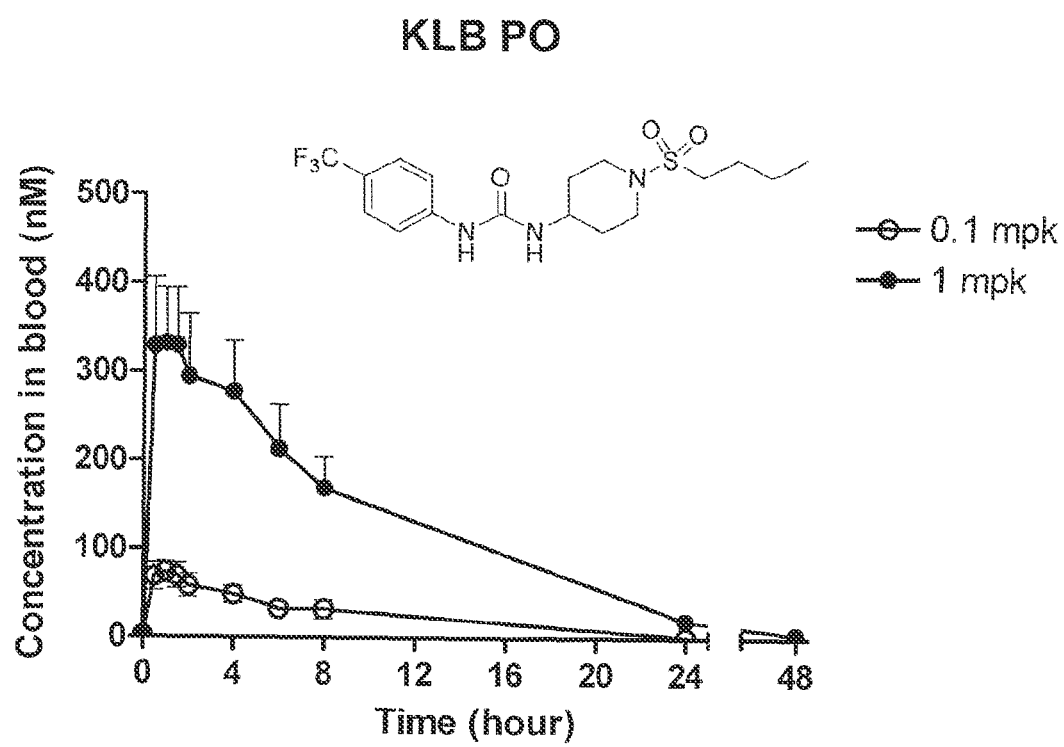
FIG. 7 shows pharmacokinetic Profile of UC2414 (KLB) in rat. Rats are treated with UC2414 by oral gavage. UC2414 was dissolved in 20% PEG in oleic acid-rich triglyceride. The result is an average of 6 rats.
Figure 8:
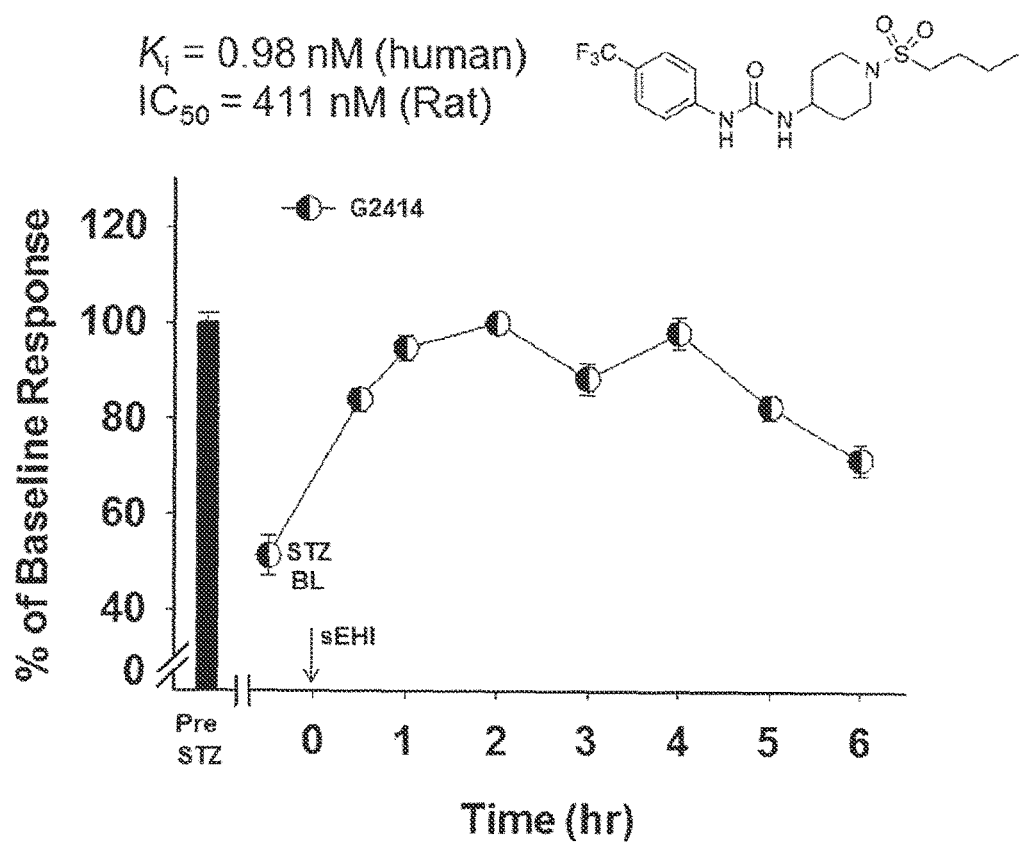
FIG. 8 shows dose (1 mpk) and time dependency of effect of UC2414 on streptozocin (STZ)-induced type I diabetes model of neuropathic pain in rats where below 60% of baseline is painful state and 100% of baseline is lack of enhanced pain detection. Rats were treated with UC2414 by oral gavage. UC2414 was dissolved in pure PEG400. (Result is an average of 6 rats).
Figure 9:
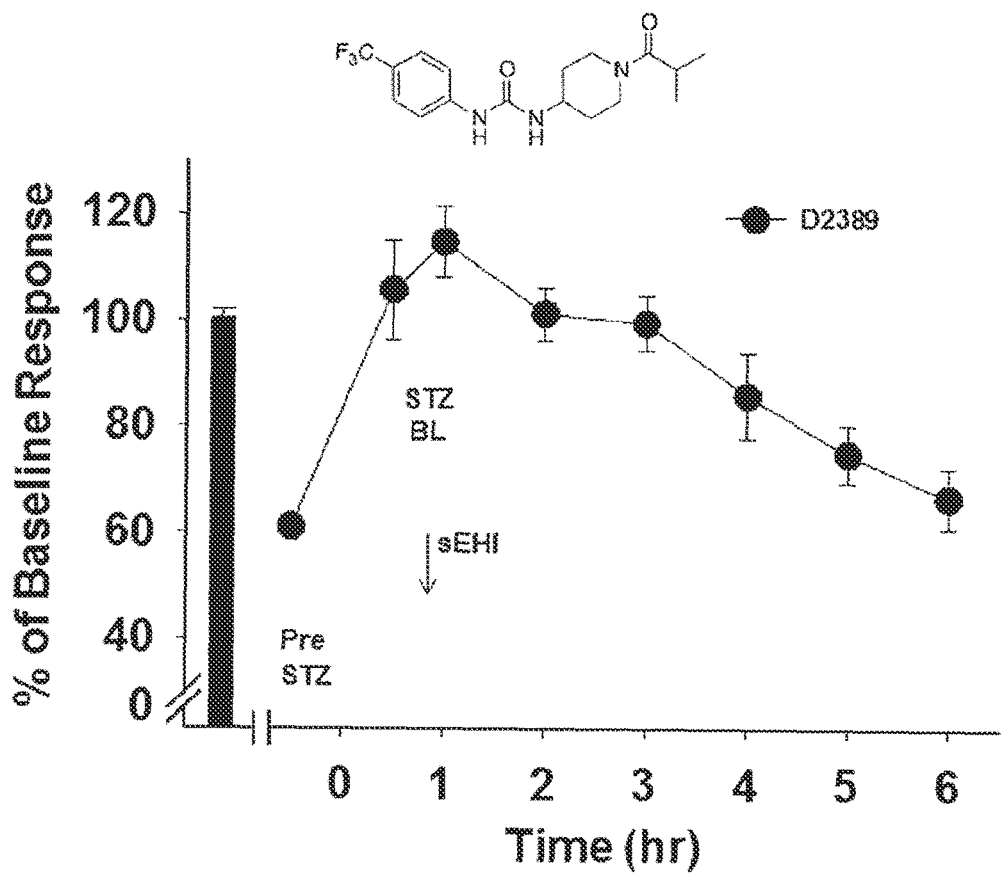
FIG. 9 shows dose (1 mpk) and time dependency of effect of UC2389 on streptozocin (STZ)-induced type I diabetes model of neuropathic pain in rats where below 60% of baseline is painful state and 100% of baseline is lack of enhanced pain detection. Rats were treated with UC2389 by oral gavage. UC2389 was dissolved in pure PEG400. (Result is an average of 6 rats)
Figure 10:
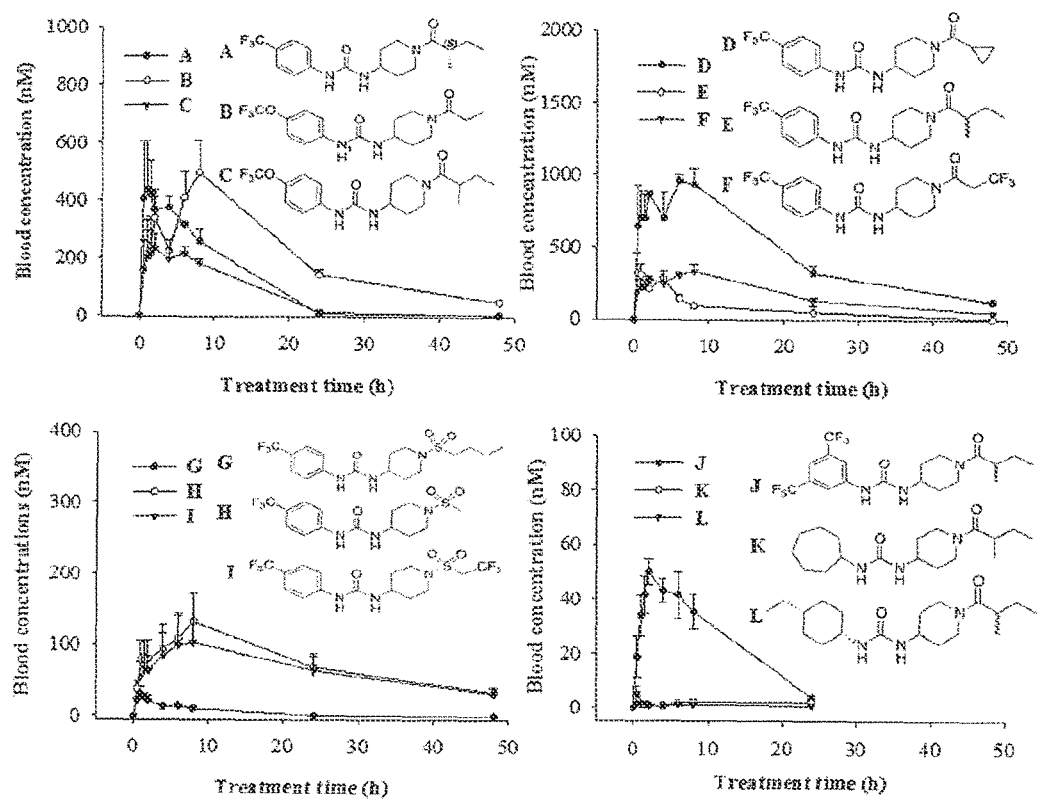
FIG. 10 shows pharmacokinetic Profile of different sEH inhibitor in mice. Mice are treated in a cassette of three inhibitors by oral gavage. Inhibitors were dissolved in 20% PEG in oleic acid-rich triglyceride. The result is an average of 6 mice.
Figure 11:
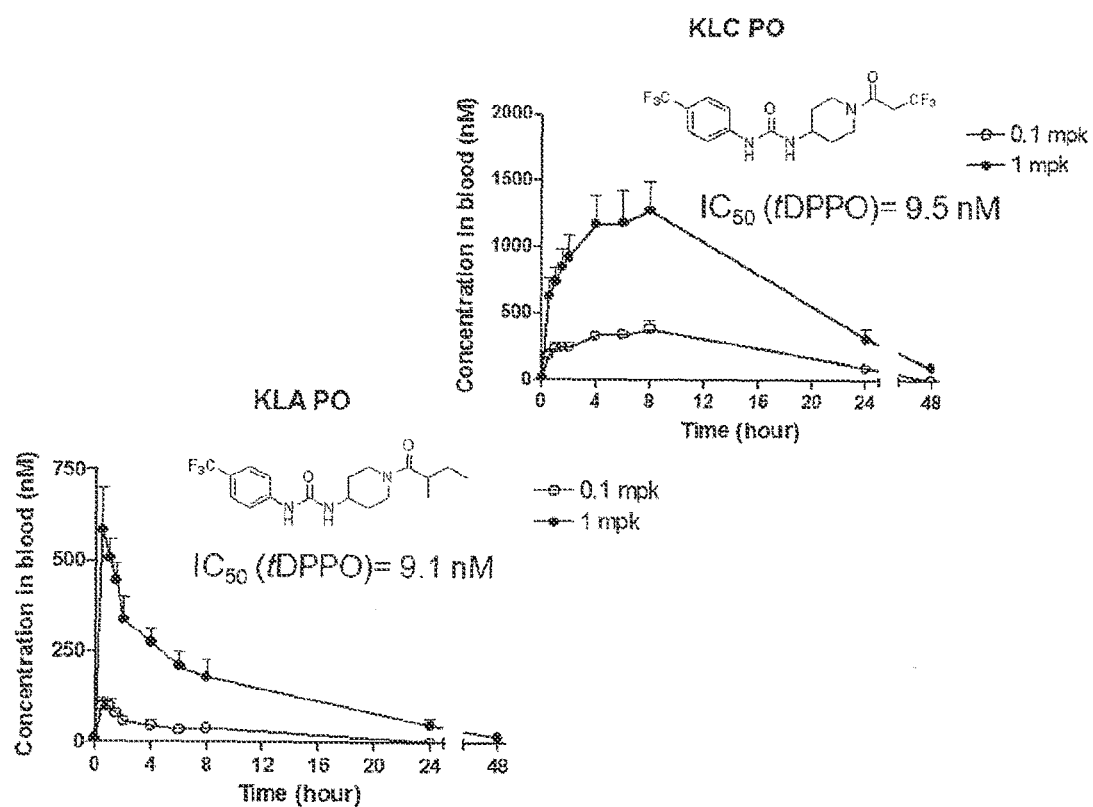
FIG. 11 shows pharmacokinetic Profile of UC2695 (KLC) and UC2383 (KLA) in rat. Rats art treated with UC2695 (KLC) and UC2383 (KLA) by oral gavage. UC2695 (KLC) and UC2383 (KLA) were dissolved in 20% PEG in oleic acid-rich triglyceride. The result is an average of 6 rats.
Figure 12:
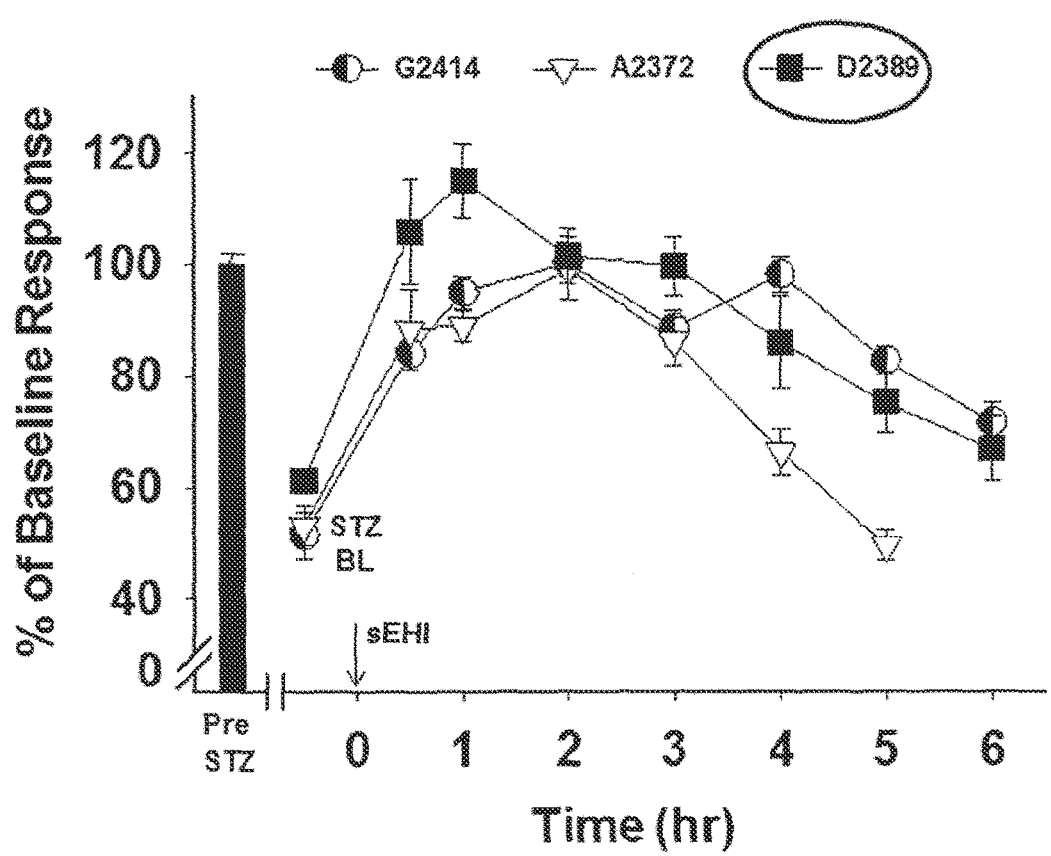
FIG. 12 shows dose (1 mpk) and time dependency of effect of UC2414, UC2372 and UC2389 on streptozocin (STZ)-induced type I diabetes model of neuropathic pain in rats where below 60% of baseline is painful state and 100% of baseline is lack of enhanced pain detection. Rats were treated with drug by oral gavage. Drugs were dissolved in pure PEG400. (Result is an average of 6 rats.)
Figure 13:
FIG. 13 shows $IC_{50}$ of inhibitors from LC/MS-MS assay using 14,15-EET as substrate with human and rat sEH.
Figure 13:
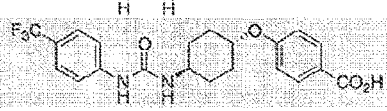
Figure 13:
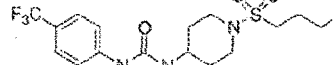
Figure 13:
Figure 14:
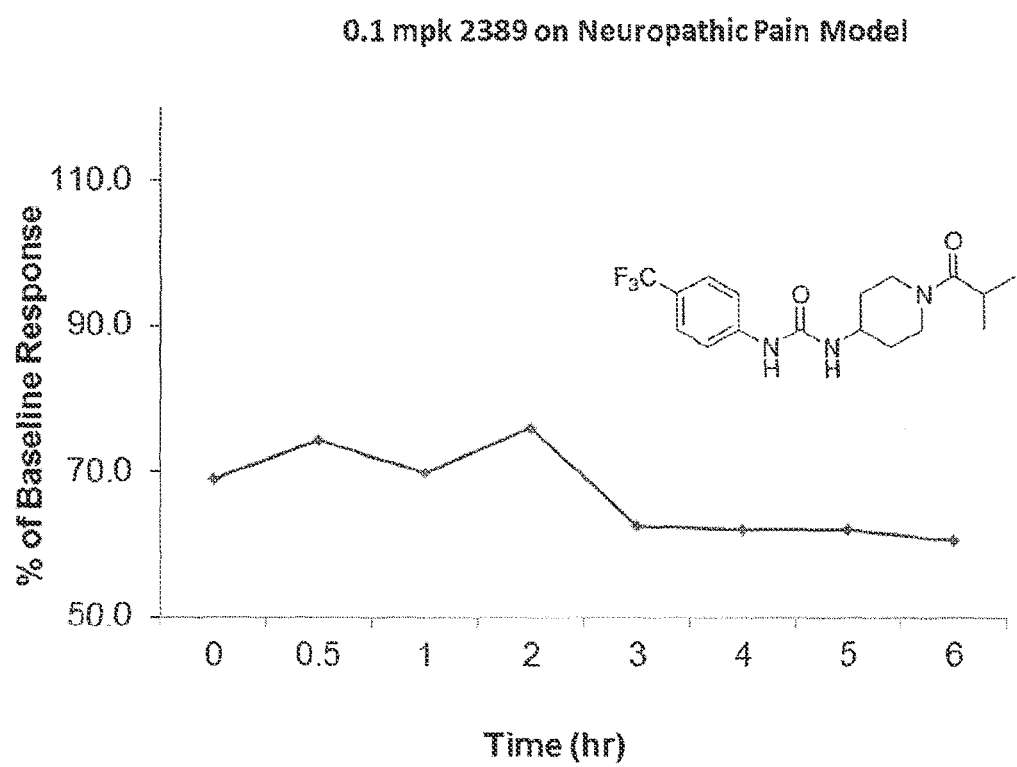
FIG. 14 shows dose (0.1 mpk) and time dependency effect of UC2389 on streptozocin (STZ)-induced type I diabetes model of neuropathic pain in rats where below 60% of baseline is painful state and 100% of baseline is lack of enhanced pain detection. Rats were treated with UC2389 by oral gavage. UC2389 was dissolved in 20% PEG in oleic acid-rich triglyceride. (Result is an average of 6 rats.)
Figure 15:
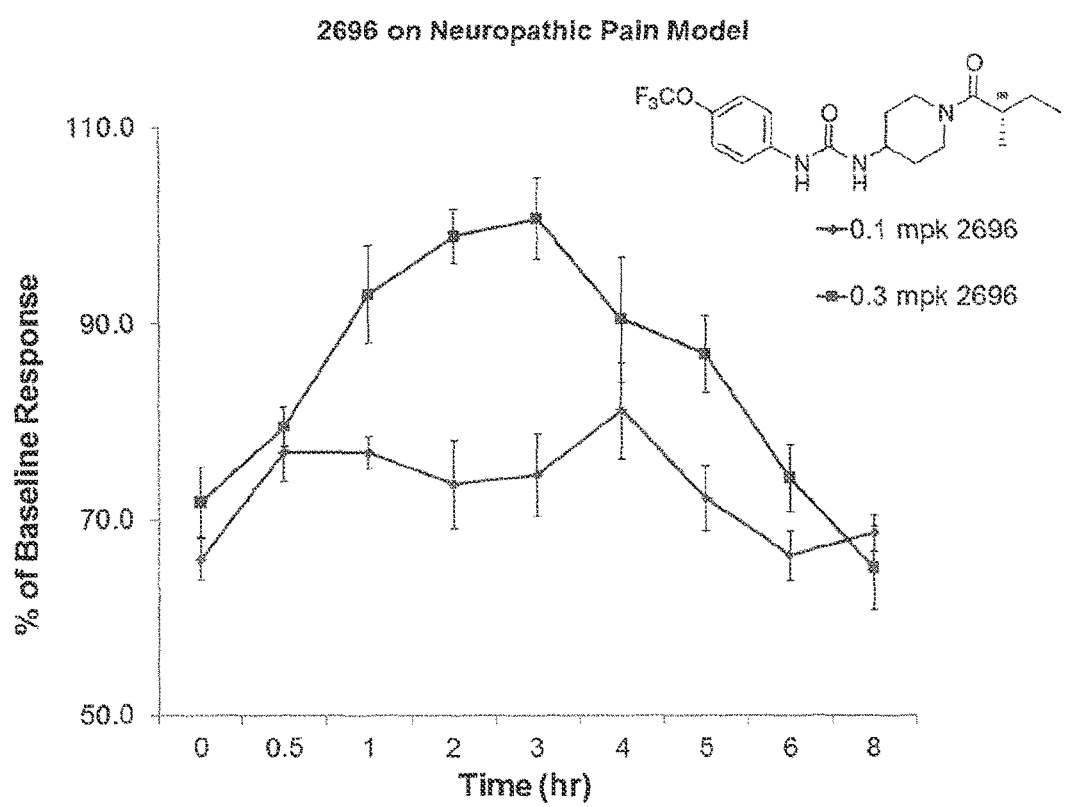
FIG. 15 shows dose (0.1 and 0.3 mpk) and time dependency effect of UC2696 on streptozocin (STZ)-induced type I diabetes model of neuropathic pain in rats where below 60% of baseline is painful state and 100% of baseline is lack of enhanced pain detection. Rats were treated with UC2696 by oral gavage. UC2696 was dissolved in 20% PEG in oleic acid-rich triglyceride. (Result is an average of 6 rats.)
Figure 16:
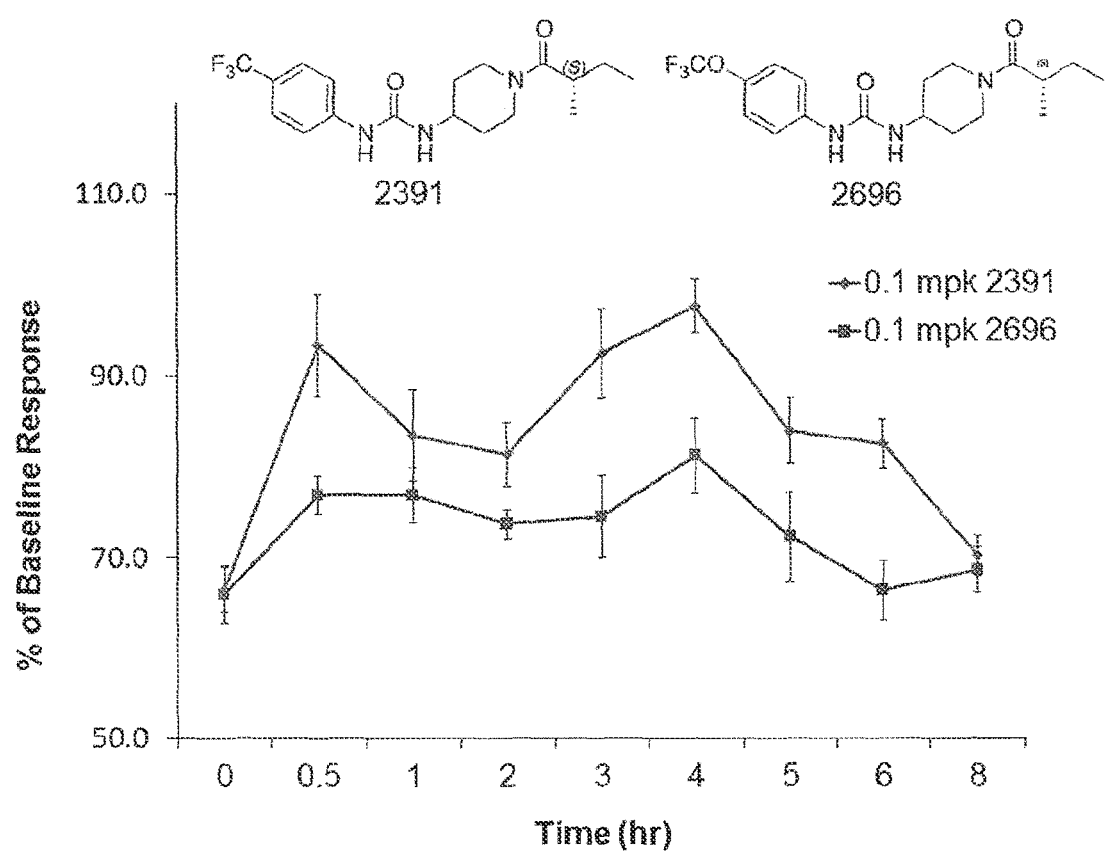
FIG. 16 shows dose (0.1 mpk) and time dependency effect of UC2391 and UC2696 on streptozocin (STZ)-induced type I diabetes model of neuropathic pain in rats where below 60% of baseline is painful state and 100% of baseline is lack of enhanced pain detection. Rats were treated with UC2391 and 2696 by oral gavage. UC2391 and 2696 were dissolved in 20% PEG in oleic acid-rich triglyceride. (Result is an average of 6 rats.)

The enzyme "soluble epoxide hydrolase" ("sEH") acts on an important branch of the arachidonic acid pathway degrading anti-inflammatory and analgesic metabolites. cis-Epoxyeicosatrienoic acids" ("EETs") are biomediators synthesized by cytochrome P450 epoxygenases, and are hydrolyzed by sEH into the corresponding diols, which are pro-inflammatory. EETs and inhibitors of sEH, sometimes (the term "sEH inhibitors" is sometimes abbreviated herein as "sEHI") have been previously found to be useful as anti-inflammatories.

Surprisingly, we have now found that sEHI are also useful to relieve neuropathic pain. We used a well-established method of quantifying pain in a well known model for neuropathic pain to elucidate the effects of inhibiting sEH and thus increasing the physiological concentration of EETs and/or other molecules containing epoxide functionality on pain perception. We demonstrated that sEH inhibitors surprisingly through a previously little known mechanism decrease the pain perception of treated animals that are suffering from neuropathic pain. Inhibitors of sEH, EETs and/or polyunsaturated fatty acids like molecules containing epoxide functionality and precursors thereof such as 2-arachidonylglycerol, ethanolamides of epoxy lipids and/or a combination thereof offer unique advantages as standalone therapeutic agents in treating, ameliorating, relieving, reducing, and/or inhibiting neuropathic pain. We show that sEH inhibitors are analgesic and have a wide therapeutic efficacy in the treatment and management of neuropathic pain, including chronic neuropathic pain, including central and peripheral neuropathic pain.

The model of neuropathic pain used is generally accepted as not involving inflammatory processes. This is because chemical and molecular analysis shows no upregulation of cyclooxygenases enzymes, and well known anti-inflammatory agents such as COX inhibitors are not effective in reducing neuropathic pain. Because sEHI inhibitors were very effective in reducing inflammatory and nociceptive pain and because sEHIs decrease the release of key pain producing prostanoid PGE2, we hypothesized that sEH inhibitors would be ineffective in reducing neuropathic pain.

Neuropathy was induced by injecting animals with a bacterial toxin (streptozocin) that is known to kill the pancreatic beta cells, thus preventing the production of insulin, the key peptide regulating blood glucose levels. The result is that the animals have high plasma levels of glucose and become diabetic, with a concomitant neuropathic pain state. This neuropathy is unrelated to the inflammatory pain states that are driven by arachidonic acid release and production of prostaglandins and other inflammatory mediators. We then measured the pain thresholds of these animals before and after the induction of neuropathy using clinically relevant pain quantification methods and subsequently intervened with sEH inhibitors.

II. Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to tight in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethane refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Representative cycloalkylene groups include, but are not limited to, cyclopropylene, cyclobutylene, cyclopentylene, cyclohexylene, and cyclooctylene. Cycloalkylene groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

"Hydrate" refers to a compound that is complexed to at least one water molecule. The compounds of the present invention can be complexed with from 1 to 10 water molecules.

"cis-Epoxyeicosatrienoic acids" ("EETs") are biomediators synthesized by cytochrome P450 epoxygenases. As discussed further below, while the use of unmodified EETs is the most preferred, derivatives of EETs, such as amides and esters (both natural and synthetic), EETs analogs, and EETs optical isomers can all be used in the methods of the invention, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides. The addition of water to the epoxides results in the corresponding 1,2-diols (Hammock, B. D. et al., in Comprehensive Toxicology: Biotransformation (Elsevier, New York), pp. 283-305 (1997); Oesch, F. Xenobiotica 3:305-340 (1972)). Four principal EH's are known: leukotriene epoxide hydrolase, cholesterol epoxide hydrolase, microsomal EH ("mEH"), and soluble EH ("sEH," previously called cytosolic EH). The leukotriene EH acts on leukotriene A4, whereas the cholesterol EH hydrates compounds related to the 5,6-epoxide of cholesterol. The microsomal epoxide hydrolase metabolizes monosubstituted, 1,1-disubstituted, cis-1,2-disubstituted epoxides and epoxides on cyclic systems to their corresponding diols. Because of its broad substrate specificity, this enzyme is thought to play a significant role in ameliorating epoxide toxicity. Reactions of detoxification typically decrease the hydrophobicity of a compound, resulting in a more polar and thereby excretable substance.

"Soluble epoxide hydrolase" ("sEH") is an epoxide hydrolase which in many cell types converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). NCBI Entrez Nucleotide accession number L05779 sets forth the nucleic acid sequence encoding the protein, as well as the 5' untranslated region and the 3' untranslated region. The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Soluble EH is only very distantly related to mEH and hydrates a wide range of epoxides not on cyclic systems. In contrast to the role played in the degradation of potential toxic epoxides by mEH, sEH is believed to play a role in the formation or degradation of endogenous chemical mediators. Unless otherwise specified, as used herein, the terms "soluble epoxide hydrolase" and "sEH" refer to human sEH.

Unless otherwise specified, as used herein, the terms "sEH inhibitor" (also abbreviated as "sEHI") or "inhibitor of sEH" refer to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now known in many species, including humans. As used herein, it refers to exogenously administered miRNA unless specifically noted or otherwise required by context.

The term "co-administration" refers to the presence of both active agents in the blood at the same time. Active agents that are co-administered can be delivered concurrently (i.e., at the same time) or sequentially.

The terms "patient," "subject" or "individual" interchangeably refers to a mammal, for example, a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The terms "reduce," "inhibit," "relieve," "alleviate" refer to the detectable decrease in symptoms of neuropathic pain, as determined by a trained clinical observer. A reduction in neuropathic pain can be measured by self-assessment (e.g., by reporting of the patient), by applying pain measurement assays well known in the art (e.g., tests for hyperalgesia and/or allodynia), and/or objectively (e.g., using functional magnetic resonance imaging or f-MRI). Determination of a reduction of neuropathic pain can be made by comparing patient status before and after treatment.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

III. Method of Relieving Neuropathic Pain

The present invention provides methods of relieving neuropathic pain by administering to a subject in need thereof, a therapeutically effective amount of an sEH inhibitor, thereby relieving the neuropathic pain.

In some embodiments, the person being treated with the she inhibitor is not being treated for atherosclerosis, other inflammatory conditions, or other conditions in which inhibition of adhesion molecule expression, particularly on endothelial cells, is desirable.

A. Inhibitors of sEH

Inhibitors of sEH useful in the methods of the present invention include any suitable sEH inhibitor. In some embodiments, the sEH inhibitor can be a compound of formula I:

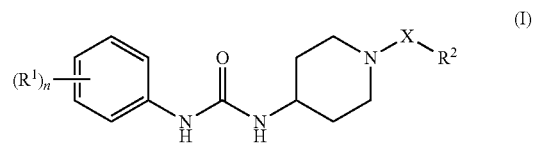

(I)

wherein each $R^1$ can independently be H, halogen, $C_{1-6}$ alkyl, $C_{1-6}$ alkoxy, $C_{1-6}$ haloalkyl, $C_{1-6}$ haloalkoxy, —O-aryl, heterocycloalkyl having 5-6 ring members and at least 1 N heteroatom and 1 O heteroatom as ring members, —OH, —NO$_2$ or —C(O)OR$^3$, wherein at least 1 $R^1$ is other than H; X can be —C(O)— or —S(O)$_2$—; $R^2$ can be $C_{2-6}$ alkyl, $C_{1-6}$ haloalkyl, cycloalkyl having 3-6 ring members, $C_{1-6}$ alkyl-heterocycloalkyl having from 5-6 ring members and at least 2 N heteroatoms as ring members and substituted with a member that can be benzyl or —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen; $R^3$ can be H or $C_{1-6}$ alkyl; subscript n can be an integer from 1 to 5; such that when $R^1$ is 4-OCF$_3$, then $R^2$ can be $C_{2-6}$ alkyl, $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member that can be benzyl or —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen; or salts and isomers thereof.

In some embodiments, each $R^1$ can be halogen, $C_{2-6}$ haloalkyl, or $C_{1-6}$ haloalkoxy. In other embodiments, each $R^1$ can be F, Cl, Br, I, CF$_3$, CF$_2$CF$_3$, CF(CF$_3$)$_2$, CH(CF$_3$)$_2$, or OCF$_3$. In some other embodiments, each $R^1$ can be Cl, CF$_3$, or OCF$_3$. In still other embodiments, each $R^1$ can be CF$_3$, or OCF$_3$.

In some embodiments, $R^2$ can be $C_{2-6}$ alkyl, $C_{1-6}$ haloalkyl, or cycloalkyl having 3-6 ring members. In other embodiments, $R^2$ can be ethyl, propyl, isopropyl, butyl, sec-butyl, isobutyl, tert-butyl, pentyl, pent-2-yl, pent-3-yl, iso-pentyl, neopentyl, hexyl, CF$_3$, CH$_2$CF$_3$, (CH$_2$)$_2$CF$_3$, cyclopropyl, cyclobutyl, cyclopentyl or cyclohexyl. In some other embodiments, $R^2$ can be isopropyl, sec-butyl, (S)-sec-butyl, pent-3-yl, or cyclopropyl. In still other embodiments, $R^2$ can be isopropyl or (S)-sec-butyl.

In some embodiments, X can be —C(O)—. In other embodiments, X can be —S(O)$_2$—.

In some embodiments, the compound can be any of the following formulas:

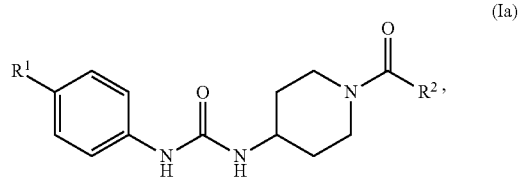

(Ia)

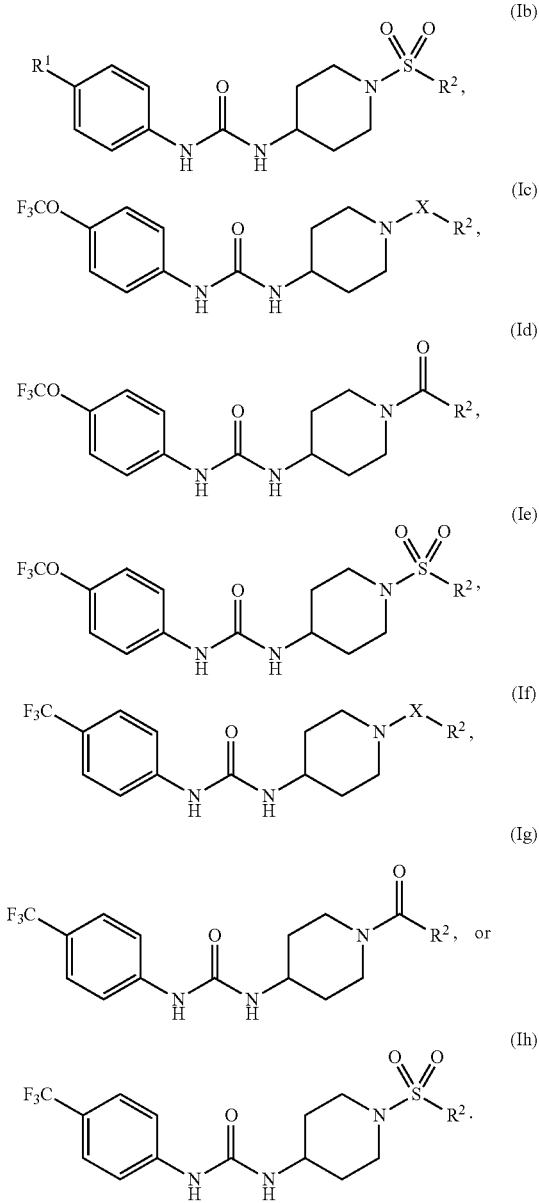

In some embodiments, the compound can be any of the following:
1-(1-isobutyrylpiperidin-4-yl)-3-(4-(trifluoromethyl)phenyl)urea,
(S)-1-(1-(2-methylbutanoyl)piperidin-4-yl)-3-(4-(trifluoromethyl)phenyl)urea,
1-(1-(butylsulfonyl)piperidin-4-yl)-3-(4-(tri fluoromethoxy)phenyl)urea, or
(S)-1-(1-(2-methylbutanoyl)piperidin-4-yl)-3-(4-(trifluoromethoxy)phenyl)urea.

In other embodiments, the compound can be any of the following:
1-(1-isobutyrylpiperidin-4-yl)-3-(4-(trifluoromethyl)phenyl)urea,
(S)-1-(1-(2-methylbutanoyl)piperidin-4-yl)-3-(4-(trifluoromethyl)phenyl)urea, or
(S)-1-(1-(2-methylbutanoyl)piperidin-4-yl)-3-(4-(trifluoromethoxy)phenyl)urea.

Prodrug versions of the compounds of the present invention are also useful, and refer to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

Preferably, the inhibitor inhibits sEH without also significantly inhibiting microsomal epoxide hydrolase ("mEH"). Preferably, at concentrations of 500 μM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 500 μM. Inhibitors with an $IC_{50}$ of less than 500 μM are preferred, with $IC_{50}$s of less than 100 μM being more preferred and, in order of increasing preference, an IC50 of 50 μM, 40 μM, 30 μM, 25 μM, 20 μM, 15 μM, 10 μM, 5 μM, 3 μM, 2 μM, 1 μM, 750 nM, 500 nM, 400 nM, 300 nM, 200 nM, 100 nM, 75 nM, 50 nM, 40 nM, 30 nM, 25 nM, 20 nM, 15 nM, 10 nM or even less being still more preferred. Assays for determining sEH activity are known in the art and described elsewhere herein.

B. Assays for Epoxide Hydrolase Activity

Any of a number of standard assays for determining epoxide hydrolase activity can be used to determine inhibition of sEH. For example, suitable assays are described in Gill., et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

C. Assay for Neuropathic Pain Activity

Neuropathic pain activity for the compounds of the present invention can be determined using any assay known in the art. For example, rats can pretreated with streptozocin to induced neuropathy. The pain threshold can be measured before (Basal level) and after streptozocin treated (Disease state). The neuropathy can be unrelated to any inflammatory pain states. The rats can then be treated with sEH inhibitors and their pain threshold measured throughout the course of treatment and compared with the basal level.

D. Patient Population

The present methods find use in treating, i.e., reducing, relieving, alleviating, ameliorating, or inhibiting neuropathic pain in a subject or patient in need thereof. The patient may be subject to suffering neuropathic pain chronically or intermittently. The patient may or may not be exhibiting or experiencing symptoms of neuropathic pain at the time of treatment. The neuropathic pain may be centrally or peripherally mediated.

Neuropathic pain results from a pathology in the nervous system. Notable features of neuropathic pain include (1) widespread pain not otherwise explainable; (2) evidence of sensory deficit; (3) burning pain; (4) pain to light stroking of the skin (allodynia); and (5) enhanced stimulus-dependent pain (hyperalgesia) and (6) attacks of pain without seeming provocation (stimulus-independent pain). Mechanisms of neuropathic pain are described, for example, in Zhuo, *Molecular Pain* (2007) 3:14; Campbell and Meyer, *Neuron* (2006) 52(1):77-92; Dworkin, et al., *Arch Neurol* (2003) 60:1524-34.

Neuropathic pain originates from a lesion of the nervous system. Any of a number of disease conditions or injuries can be the underlying cause of neuropathic pain. For example, the patient may be suffering from a metabolic disease (e.g., diabetic neuropathy), an autoimmune disease (e.g., multiple sclerosis), a viral infection (e.g., shingles and sequelae, postherpetic neuralgia), vascular disease (e.g., stroke), trauma and/or cancer. See, e.g., Campbell and Meyer, *Neuron* (2006) 52(1):77-92; Dworkin, et al., *Arch Neurol* (2003) 60:1524-34.

In some embodiments, the patient is suffering from peripheral neuropathic pain, for example, as a result of a disease condition including acute and chronic inflammatory demyelinating polyradiculoneuropathy; alcoholic polyneuropathy; chemotherapy-induced polyneuropathy; complex regional pain syndrome; entrapment neuropathies (e.g., carpal tunnel syndrome); HIV sensory neuropathy; iatrogenic neuralgias (e.g., postmastectomy pain or postthoracotomy pain); idiopathic sensory neuropathy; nerve compression or infiltration by tumor; nutritional deficiency-related neuropathies; painful diabetic neuropathy; phantom limb pain; postherpetic neuralgia; postradiation plexopathy; radiculopathy (cervical, thoracic, or lumbosacral); toxic exposure-related neuropathies; tic douloureux (trigeminal neuralgia); and/or posttraumatic neuralgias.

In some embodiments, the patient is suffering from central neuropathic pain, for example, as a result of a disease condition including compressive myelopathy from spinal stenosis; HIV myelopathy, multiple sclerosis-related pain; Parkinson disease-related pain; postischemic myelopathy; postradiation myelopathy; poststroke pain; posttraumatic spinal cord injury pain; and/or syringomyelia.

Neuropathic pain is distinguished from inflammatory pain in that it is not mediated by arachidonic acid, cyclooxygenases and prostaglandins. Therefore, neuropathic pain is not reduced or alleviated by non-steroidal anti-inflammatory agents, e.g., inhibitors of cyclooxygenases ("COX"), including selective COX-2 inhibitors.

In some embodiments of the invention, the person being treated with sEHI does not have hypertension or is not currently being treated with an anti-hypertension agent that is an inhibitor of sEH. In some embodiments, the person being treated does not have inflammation or, if he or she has inflammation, has not been treated with an sEH inhibitor as an anti-inflammatory agent. In some preferred embodiments, the person is being treated for inflammation but by an anti-inflammatory agent, such as a steroid, that is not an inhibitor of sEH. Whether or not any particular anti-inflammatory or anti-hypertensive agent is also a sEH inhibitor can be readily determined by standard assays, such as those taught in U.S. Pat. No. 5,955,496.

In some embodiments, the patient's disease or condition is not caused by an autoimmune disease or a disorder associated with a T-lymphocyte mediated immune function autoimmune response. In some embodiments, the patient does not have a pathological condition selected from type 1 or type 2 diabetes, insulin resistance syndrome, atherosclerosis, coronary artery disease, angina, ischemia, ischemic stroke, Raynaud's disease, or renal disease.

In some embodiments, the patient is not a person with diabetes mellitus whose blood pressure is 130/80 or less, a person with metabolic syndrome whose blood pressure is less than 130/85, a person with a triglyceride level over 215 mg/dL, or a person with a cholesterol level over 200 mg/dL, or is a person with one or more of these conditions who is not taking an inhibitor of sEH. In some embodiments, the patient does not have an obstructive pulmonary disease, an interstitial lung disease, or asthma.

In some embodiments, the patient is not also currently being treated with an inhibitor of one or more enzymes selected from the group consisting of cyclo-oxygenase ("COX")-1, COX-2, and 5-lipoxygenase ("5-LOX"), or 5-lipoxygenase activating protein ("FLAP"). It is noted that many people take a daily low dose of aspirin (e.g., 81 mg) to reduce their chance of heart attack, or take an occasional aspirin to relieve a headache. Persons taking low dose aspirin to reduce the risk of heart attack are not currently known to take that aspirin in combination with an sEHI to potentiate that effect. It is also contemplated that persons taking an occasional aspirin or ibuprofen tablet to relieve a headache or other episodic minor aches or pain would not ordinarily take that tablet in combination with an sEHI to potentiate that pain relief. In some embodiments, therefore, the patient being treated by the methods of the invention may have taken an inhibitor of COX-1, COX-2, or 5-LOX in low doses, or taken such an inhibitor on an occasional basis to relieve an occasional minor ache or pain.

In some embodiments, the patient does not have dilated cardiomyopathy or arrhythmia.

In some embodiments, the patient is not applying sEHI topically for pain relief. In some embodiments, the patient is not administering sEHI topically to the eye to relieve, for example, dry eye syndrome or intraocular pressure. In some embodiments, the patient does not have glaucoma or is being treated for glaucoma with agents that do not also inhibit sEH.

In some embodiments, the patient does not suffer from anxiety, panic attacks, agitation, status epilepticus, other forms of epilepsy, symptoms of alcohol or opiate withdrawal, insomnia, or mania. In some embodiments, the patient has one of these conditions, but is not being treated for the condition with an sEHI.

In some embodiments, the patient is not being treated for cancer of cells expressing peripheral benzodiazepine receptors (PBR) or $CB_2$ receptors. In some embodiments, a patient being treated for a cancer expressing such receptors is not being treated with an sEHI.

In some embodiments, the patient is not being treated to reduce oxygen radical damage. In some embodiments, a patient being treated to reduce oxygen radical damage is not being treated with an sEHI.

In some embodiments, the patient is not being treated for irritable bowel syndrome. In some embodiments, a patient being treated for irritable bowel syndrome is not being treated with an sEHI.

IV. Administration

Inhibitors of sEH can be prepared and administered in a wide variety of oral, parenteral and aerosol formulations. In some preferred forms, compounds for use in the methods of the present invention can be administered by injection, that is, intravenously, intramuscularly, intracutaneously, subcutaneously, intradermally, intrathecally, intraduodenally, or intraperitoneally, while in others, they are administered orally. Administration can be systemic or local, as desired. The sEH inhibitors can also be administered by inhalation. Additionally, the sEH inhibitors can be administered transdermally. Accordingly, the methods of the invention permit administration of pharmaceutical compositions comprising a pharmaceutically acceptable carrier or excipient and either a selected inhibitor or a pharmaceutically acceptable salt of the inhibitor.

For preparing pharmaceutical compositions from sEH inhibitors pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of the sEH inhibitor is employed in reducing, alleviating, relieving, ameliorating, preventing and/or inhibiting neuropathic pain. The dosage of the specific compound for treatment depends on many factors that are well known to those skilled in the art. They include for example, the route of administration and the potency of the particular compound.

Determination of an effective amount is well within the capability of those skilled in the art. Generally, an efficacious or effective amount of a sEH inhibitor is determined by first administering a low dose or a small amount of either a sEH inhibitor, and then incrementally increasing the administered dose or dosages, adding a second medication as needed, until a desired effect of is observed in the treated subject with minimal or no toxic side effects. An exemplary dose is from about 0.001 µM/kg to about 100 mg/kg body weight of the mammal. sEH inhibitors with lower IC50 concentrations can be administered in lower doses.

In another set of embodiments, an sEH inhibitor is administered by delivery to the nose or to the lung. Intranasal and pulmonary delivery are considered to be ways drugs can be rapidly introduced into an organism. Devices for delivering drugs intranasally or to the lungs are well known in the art. The devices typically deliver either an aerosol of an therapeutically active agent in a solution, or a dry powder of the agent. To aid in providing reproducible dosages of the agent, dry powder formulations often include substantial amounts of excipients, such as polysaccharides, as bulking agents.

Detailed information about the delivery of therapeutically active agents in the form of aerosols or as powders is available in the art. For example, the Center for Drug Evaluation and Research ("CDER") of the U.S. Food and Drug Administration provides detailed guidance in a publication entitled: "Guidance for Industry: Nasal Spray and Inhalation Solution, Suspension, and Spray Drug Products—Chemistry, Manufacturing, and Controls Documentation" (Office of Training and Communications, Division of Drug Information, CDER, FDA, July 2002). This guidance is available in written form from CDER, or can be found on-line by entering "http://www." followed by "fda.gov/cder/guidance/4234fnl.htm". The FDA has also made detailed draft guidance available on dry powder inhalers and metered dose inhalers. See, Metered Dose Inhaler (MDI) and Dry Powder Inhaler (DPI) Drug Products—Chemistry, Manufacturing, and Controls Documentation, 63 Fed. Reg. 64270, (November 1998). A number of inhalers are commercially available, for example, to administer albuterol to asthma patients, and can be used instead in the methods of the present invention to administer the sEH inhibitor, EET, or a combination of the two agents to subjects in need thereof.

In some aspects of the invention, the sEH inhibitor is dissolved or suspended in a suitable solvent, such as water, ethanol, or saline, and administered by nebulization. A nebulizer produces an aerosol of fine particles by breaking a fluid into fine droplets and dispersing them into a flowing stream of gas. Medical nebulizers are designed to convert water or aqueous solutions or colloidal suspensions to aerosols of fine, inhalable droplets that can enter the lungs of a patient during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/mL.

Nebulizers for delivering an aerosolized solution to the lungs are commercially available from a number of sources, including the AERx™ (Aradigm Corp., Hayward, Calif.) and the Acorn II® (Vital Signs Inc., Totowa, N.J.).

Metered dose inhalers are also known and available. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; and 4,896,832.

The formulations may also be delivered using a dry powder inhaler (DPI), i.e., an inhaler device that utilizes the patient's inhaled breath as a vehicle to transport the dry powder drug to the lungs. Such devices are described in, for example, U.S. Pat. Nos. 5,458,135; 5,740,794; and 5,785,049. When administered using a device of this type, the powder is contained in a receptacle having a puncturable lid or other access surface, preferably a blister package or cartridge, where the receptacle may contain a single dosage unit or multiple dosage units. Other dry powder dispersion devices for pulmonary administration of dry powders include those described in Newell, European Patent No. EP 129985; in Hodson, European Patent No. EP 472598, in Cocozza, European Patent No. EP 467172, and in Lloyd, U.S. Pat. Nos. 5,522,385; 4,668,281; 4,667,668; and 4,805,811. Dry powders may also be delivered using a pressurized, metered dose inhaler (MDI) containing a solution or suspension of drug in a pharmaceutically inert liquid propellant, e.g., a chlorofluorocarbon or fluorocarbon, as described in U.S. Pat. Nos. 5,320,094 and 5,672,581.

Without further elaboration, it is believed that one skilled in the art can, using the preceding description, practice the present invention to its fullest extent.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

V. Examples

Example 1. Diabetic Neuropathic Pain Model

Diabetic neuropathic pain was modeled using streptozocin which targets and kills the pancreatic beta islet cells rendering the animals with type I diabetes. The rats were acclimated for one hour and tested for baseline thresholds before inducing diabetes. The baseline mechanical withdrawal thresholds were established using the von Frey mechanical nociceptive test with an electronic anesthesiometer (IITC, Woodland Hills, Calif.). Subsequently, streptozocin (55 mg/kg) in saline was injected via tail vein per previously reported methods (Aley, K. O. and Levine J. D. *J. Pain* 2001, 2, 146.). After five days the allodynia of diabetic rats was confirmed with the von Frey nociceptive assay. Rats were placed in clear acrylic chambers on a steel mesh floor. The hind paw of the rat was probed through the mesh with a rigid tip probe connected to the electronic readout pressure meter set to the maximum hold setting. The withdrawal thresholds per rat were measured 3-5 times at 1 minute intervals for each time point.

The baseline diabetic allodynia was quantified again at the beginning of all test days. The rats were then administered vehicle or sEH inhibitor via oral gavage and tested at 30 min. 1, 2, 3, 4, 5, and 6 h for mechanical withdrawal thresholds. The reported scores are the grams of force required to elicit a hind paw withdrawal averaged with standard error of the mean (S.E.M.) per a group of rats (n=6). The baseline diabetic neuropathic scores are normalized to 100 percent to reflect the response to treatments which are reported as % of post diabetic neuropathic baseline.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of inhibiting a soluble epoxide hydrolase in a subject, said method comprising administering to said subject a compound selected from the group consisting of:
   (S)-1-(1-(2-methylbutanoyl)piperidin-4-yl)-3-(4-(trifluoromethoxy)phenyl)urea; and
   1-(1-(butylsulfonyl)piperidin-4-yl)-3-(4-(trifluoromethoxy)phenyl)urea,
and pharmaceutically acceptable salts thereof.

2. The method of claim 1, wherein the subject has a neuropathic pain selected from the group consisting of post-herpetic neuralgia, trigeminal neuralgia, focal peripheral nerve injury, anesthesia, dolorosa, central pain due to stroke, central pain due to mass lesion, central pain due to spinal cord injury, central pain due to multiple sclerosis, peripheral neuropathy due to diabetes, peripheral neuropathy due to human immunodeficiency virus and peripheral neuropathy due to chemotherapy.

3. The method of claim 1, wherein the subject has central neuropathic pain.

4. The method of claim 1, wherein the subject has peripheral neuropathic pain.

5. The method of claim 1, wherein the subject has a neuropathic pain at the time of administration.

6. The method of claim 1, wherein the compound is administered orally.

7. The method of claim 1, wherein the compound is administered intravenously.

8. The method of claim 1, wherein the compound is administered intrathecally.

* * * * *